(12) United States Patent
Okada et al.

(10) Patent No.: US 8,841,624 B2
(45) Date of Patent: Sep. 23, 2014

(54) RADIOGRAPHIC IMAGE DETECTOR, RADIOGRAPHIC IMAGING APPARATUS, RADIOGRAPHIC IMAGING SYSTEM

(71) Applicant: FUJIFILM Corporation, Tokyo (JP)

(72) Inventors: Yoshihiro Okada, Ashigarakami-gun (JP); Tomoki Inoue, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 112 days.

(21) Appl. No.: 13/687,113

(22) Filed: Nov. 28, 2012

(65) Prior Publication Data

US 2013/0163722 A1    Jun. 27, 2013

(30) Foreign Application Priority Data

Dec. 22, 2011    (JP) .................................. 2011-282353

(51) Int. Cl.
| | | |
|---|---|---|
| *H01L 27/146* | (2006.01) | |
| *H01L 27/00* | (2006.01) | |
| *G01T 1/24* | (2006.01) | |
| *G01N 23/04* | (2006.01) | |
| *G01T 1/00* | (2006.01) | |

(52) U.S. Cl.
CPC ................ *G01T 1/247* (2013.01); *G01N 23/04* (2013.01); *G01T 1/00* (2013.01)
USPC ................................... 250/370.09; 250/208.1

(58) Field of Classification Search
CPC .................................. G01T 1/20; G01N 23/04
USPC .......... 250/370.09, 363.02, 354.1, 208.1, 394
See application file for complete search history.

(56) References Cited

U.S. PATENT DOCUMENTS

2008/0210946 A1* 9/2008 Okada et al. .................... 257/71

FOREIGN PATENT DOCUMENTS

| JP | 2003-23555 A | 1/2003 |
| JP | 2003-255049 A | 9/2003 |
| JP | 2004-46143 A | 2/2004 |

OTHER PUBLICATIONS

Japanese Office Action, dated Nov. 12, 2013, for Japanese Application No. 2011-282353 with an English translation.

* cited by examiner

*Primary Examiner* — David Porta
*Assistant Examiner* — Abra Fein
(74) *Attorney, Agent, or Firm* — Birch, Stewart, Kolasch & Birch, LLP (57) ABSTRACT

The present invention provides a radiographic image detector that maintains even resolution in 6 directions before and after 4 pixel binning processing. In the radiographic image detector, first TFT switches of each pixel are switched ON according to control signals from plural first scan lines, and charge signals according to accumulated charges are transmitted through data lines. For each pixel group configured by combinations of plural adjacent pixels, second TFT switches of the pixels configuring each of the pixel groups are switched ON according to control signals from plural second scan lines, and binning processing is performed in which 4 pixels worth of charges are read simultaneously and are combined, and charge signals according to the amount of the combined charges are transmitted through the data lines.

14 Claims, 6 Drawing Sheets

RADIOGRAPHIC IMAGE DETECTOR, RADIOGRAPHIC IMAGING APPARATUS, RADIOGRAPHIC IMAGING SYSTEM

CROSS-REFERENCE TO RELATED APPLICATION

This application claims priority under 35 USC 119 from Japanese Patent Application No. 2011-282353, filed on Dec. 22, 2011 the disclosure of which is incorporated by reference herein.

BACKGROUND OF THE INVENTION

1. Field of the Invention

The present invention relates to a radiographic image detector, a radiographic imaging apparatus and a radiographic imaging system. The present invention particularly relates to a radiographic image detector, radiographic imaging apparatus and a radiographic imaging system for direct conversion of radiation into charges.

2. Description of the Related Art

Many radiographic image detection apparatuses recently being put into practice employ radiation detectors such as Flat Panel Detectors (FPDs) that have a X-ray-sensitive layer disposed above a Thin Film Transistor (TFT) active matrix substrate, and are capable of directly converting X-ray data into digital data. Such FPDs have the advantage of enabling more immediate image and video image confirmation than for example conventional film screens, and their use is rapidly widening. Various types of these radiation detectors are proposed. For example, direct-conversion-type in which radiation is directly converted into charges in a semiconductor layer and the charges accumulated, and indirect-conversion-type in which radiation is first converted into light by a scintillator, such as CsI: TI or GOS ($Gd_2O_2S$:Tb), and then the converted light is converted into charges in a semiconductor layer and the charges accumulated, are proposed.

In radiation detectors, for example, plural scan lines and plural signal lines are disposed intersecting with each other, and pixels are disposed in a matrix pattern corresponding to each of the intersections between the scan lines and the signal lines. The plural scan lines and the plural signal lines are connected to an external circuit peripheral to the radiation detector, for example an amplifier Integrated Circuit (IC) or a gate IC.

Reducing the size of the pixels in radiation detectors is an effective way to increase the resolution of FPDs. Particularly, in direct-conversion-type radiation detectors employing, for example, Se, various radiation detectors are proposed for high definition enhanced image quality that contribute to increasing the resolution whilst leaving the pixel size virtually unchanged. For example, products with small pixel size are proposed for FPDs for mammography where there is an emphasis on resolution.

The use of hexagonal shaped pixels in radiation detection apparatuses in order to achieve an increase in both resolution and sensitivity, is proposed (see for example Japanese Patent Application Laid-Open (JP-A) No. 2003-255049), since simply reducing the pixel size may lead to a drop in sensitivity due to the proportional relationship to surface area in a radiation detection device. With square shaped pixels, the resolution in diagonal directions is lower than in the horizontal and vertical directions. However, employing hexagonal shaped pixels may secure high resolution in each of the horizontal, vertical and diagonal directions.

When still imaging and video imaging (fluoroscopic imaging) by using the hexagonal shaped pixels described above, methods of reading charges from plural pixels at the same time and summing the obtained values (binning) shall be considered, in particular in order to maintain a high frame rate such as in video. Performing such pixel summing within a sensor must also be considered.

However, in pixel summing of plural hexagonal shaped pixels, unevenness in pixel positions (the positions of the center of gravity when plural pixels are treated as one pixel cluster) may occur before and after summing, depending on the summing method. Accordingly, even resolution in each of the horizontal, vertical and diagonal directions that has been secured in before summing may not be maintained in after summing.

SUMMARY OF THE INVENTION

The present invention provides a radiographic image detector that may maintain even resolution before and after combining the charges of plural pixels in each of the horizontal, vertical and diagonal directions.

A first aspect of the present invention is a radiographic image detector including: a detection section including plural pixels having hexagonal shaped pixel regions arrayed in a honeycomb pattern, each pixel including, a sensor portion that generates charges according to irradiated radiation, a first switching element that reads out the generated charges, and a second switching element that reads out the generated charges; plural first scan lines that are disposed one for each of respective pixel rows of the plural pixels, and that are each connected to a control terminal of the first switching elements in the corresponding pixel row; plural second scan lines that are disposed one for each of respective pairs of column direction adjacent pixel rows from the plural pixel rows, and that are each connected to a control terminal of the second switching elements in the corresponding column direction adjacent pair of pixel rows; and plural data lines that are disposed to respectively intersect with the plural first scan lines and the plural second scan lines, that transmit first charge signals corresponding to charges read out by the first switching elements in the plural pixels in response to signals output to the plural first scan lines, and that transmit second charge signals corresponding to a combined charge amount of 4 mutually adjacent pixels in a column direction adjacent pair of pixel rows read out by the second switching elements of the 4 mutually adjacent pixels in response to signals output to the plural second scan lines.

In a second aspect of the present invention, in the first aspect, the 4 pixels may configure a pixel group of repeating units of 2 successive pixels along the same pixel row direction, and 2 successive pixels along the pixel row direction of a pixel column direction adjacent pixel row to the first 2 pixels, and the 4 pixels may be configured by 3 pixels disposed such that two adjoining sides of each of the pixels are respectively mutually adjacent to one side of the remaining 2 pixels, and by 1 pixel disposed such that two adjoining sides are respectively mutually adjacent to one side of 2 pixels out of the 3 pixels.

In a third aspect of the present invention, in the second aspect, combinations of the 4 pixels configuring respective pixel groups in the plural pixel groups may be determined such that, when plural hexagonal shaped regions are formed adjacent to each other, the plural hexagonal shape regions results in a honeycomb pattern array, wherein each of the hexagonal shape regions may be formed by including inside one center of gravity of a region surrounded by an outline of the plural pixel groups configured by the respective 4 pixels, and by connecting together 6 individual centers of gravity present at the periphery of the one center of gravity.

In a fourth aspect of the present invention, in the above aspects, the hexagonal shaped pixel regions may be each formed in a regular hexagonal shape.

In a fifth aspect of the present invention, in the first to the third aspects, the hexagonal shaped pixel regions may be each formed in a flattened hexagonal shape.

In a sixth aspect of the present invention, in the fifth aspect, the hexagonal shaped pixel regions may be formed flattened such that one diagonal line out of 3 diagonal lines passing through the center of each of the pixel regions is shorter than the other two diagonal lines, and the other two diagonal lines are of equal length to each other.

In a seventh aspect of the present invention, in the first aspect, the plural data lines may be disposed bent along one portion of the hexagonal shaped pixel region periphery.

In an eighth aspect of the present invention, in the above aspects, the sensor portions may include a semiconductor film that receives irradiation of radiation and generates charges, the charges may be accumulated in a storage capacitor provided in each of the plural hexagonal shaped pixels, and the charges accumulated in the storage capacitor may be read by the first switching element and the second switching element.

In a ninth aspect of the present invention, in the first to the seventh aspects, the sensor portions may include a scintillator that converts the radiation that has been irradiated into visible light, and, after the converted visible light has been converted into charges by a semiconductor layer, the charges may be read by the first switching element and the second switching element.

In a tenth aspect of the present invention, in the eighth aspect, may further include plural common lines that connect together one electrode of each of the storage capacitors and that fixes the electrodes to a specific electrical potential.

In an eleventh aspect of the present invention, in the tenth aspect, the sensor portions, the first switching elements and the second switching elements may be disposed inside respective regions surrounded by a line segment dividing each of the pixels into two along a direction intersecting with the plural first scan lines extension direction and the plural second scan lines extension direction, and surrounded by three sides at the periphery of each of the pixels where the data lines are provided, and the plural common lines are disposed between the plural data lines without intersecting with the plural data lines.

In a twelfth aspect of the present invention, in the eleventh aspect, the plural common lines may extend between the plural data lines in a straight line shape or in a substantially straight line shape.

In a thirteenth aspect of the present invention, in the twelfth aspect, the plural common lines may be connected to the plural data lines through the storage capacitors, the first switching elements and the second switching elements.

In a fourteenth aspect of the present invention, in the thirteenth aspect, the plural first scan lines, the plural second scan lines, the plural data lines, the plural common lines, the first switching elements and the second switching elements may be disposed at a lower layer side of the sensor portions.

A fifteenth aspect of the present invention is a radiographic imaging apparatus including the radiographic image detector of any one of the above aspects, and that images a radiographic image with the radiographic image detector.

A sixteenth aspect of the present invention is a radiographic imaging system including the radiographic imaging apparatus of the above aspect, and a control section that instructs the radiographic imaging apparatus to perform imaging of a radiographic image and acquires a radiographic image from the radiographic imaging apparatus, wherein the control section includes, a switching section that, based on an external instruction, switches between first image acquisition that acquires image data in single-pixel units of a radiographic image detection element, and second image acquisition that acquires image data in multi-pixel units of the radiographic image detection element.

According to the above aspects, a radiographic image detector may maintain even resolution before and after combining the charges of pixel groups configured by plural pixels in each of the horizontal, vertical and diagonal directions.

BRIEF DESCRIPTION OF THE DRAWINGS

Exemplary embodiments of the present invention will be described in detail based on the following figures, wherein.

DETAILED DESCRIPTION OF THE INVENTION

Explanation follows regarding exemplary embodiments of the present invention, with reference to the drawings.

First Exemplary Embodiment

Figure 1:
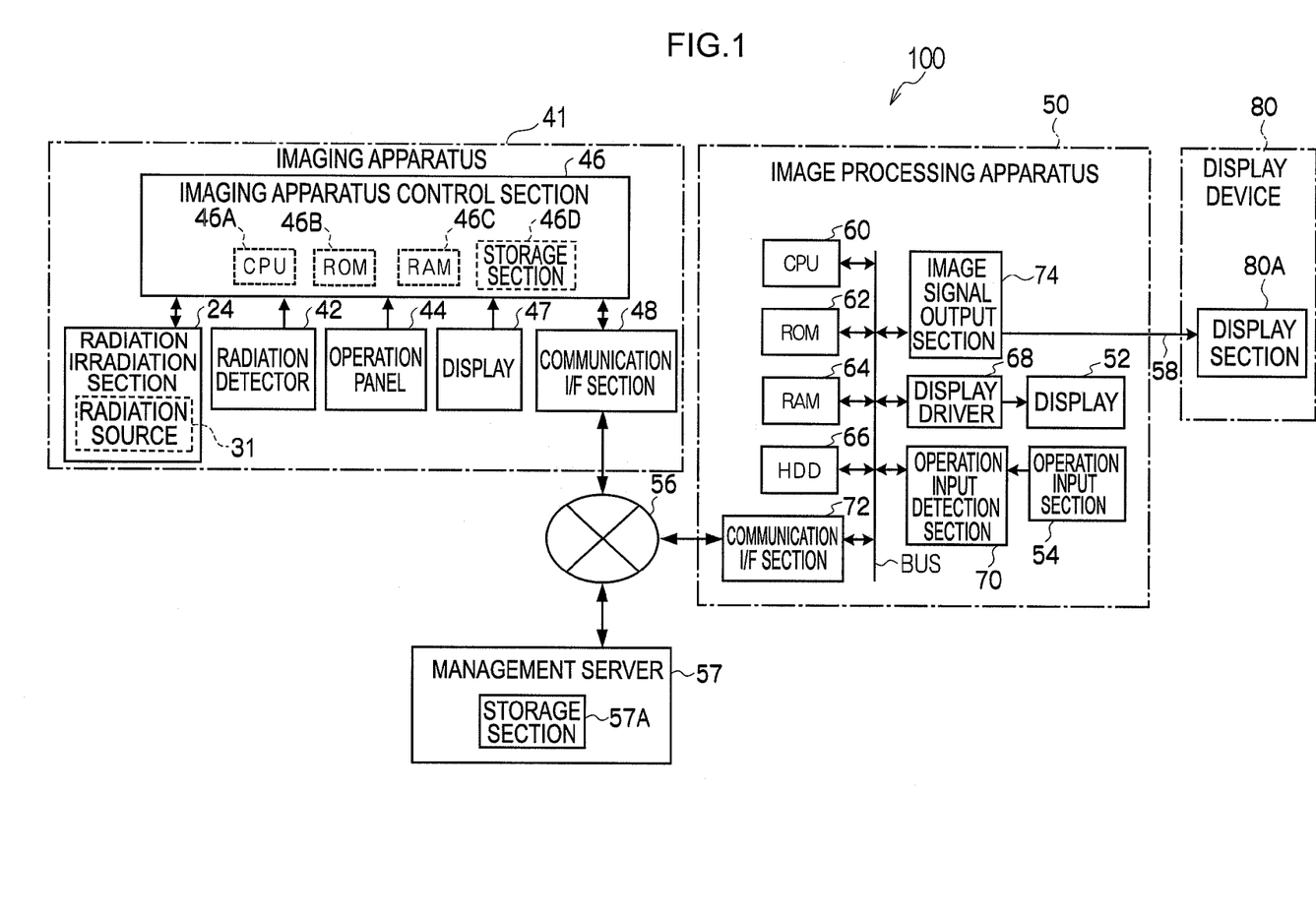
FIG. 1 is a block diagram illustrating a configuration of a radiographic imaging system according to a first exemplary embodiment of the present invention.

FIG. 1 is a block diagram illustrating a configuration of a radiographic imaging system 100 according to a first exemplary embodiment of the present invention. The radiographic imaging system 100 includes an imaging apparatus 41 that images radiographic images, an image processing apparatus 50 that performs image processing on image data expressing imaged radiographic images, and a display device 80 for displaying a subject image expressed by the image data that has been subjected to image processing.

The imaging apparatus 41 includes a radiation irradiation section 24, a radiation detector 42 that detects a radiographic image, an operation panel 44 that is input with exposure conditions including data, such as, tube voltage, tube current, irradiation duration, imaging conditions, various operation data and various operation instructions, an imaging apparatus control section 46 that controls the operation of the apparatus overall, a display 47 that displays such displays as an operation menu and various information, and a communication I/F section 48 that is connected to a network 56 such as a LAN and that transmits and receives various data to and from other devices connected to the network 56. The imaging apparatus 41 according to the present exemplary embodiment is configured capable of switching between a video imaging mode that successively images radiographic images (video imaging) and a still imaging mode that performs still imaging. The imaging mode can be input as one of the imaging conditions to the imaging apparatus 41 from the operation panel 44. The imaging apparatus 41 performs video imaging or still imaging according to the imaging mode input through the operation panel 44.

The imaging apparatus control section 46 includes a CPU 46A, ROM 46B, RAM 46C and a non-volatile storage section 46D configured, for example, from a HDD or flash memory. The imaging apparatus control section 46 is connected to the radiation irradiation section 24, the radiation detector 42, the operation panel 44, the display 47 and the communication I/F section 48 through a bus (not shown in the drawings). Programs, such as a program for execution by the CPU 46A, are stored in the storage section 46D. Data such as image data (digital data) expressing radiographic images is stored in the storage section 46D. For example, when the imaging apparatus 41 of the present exemplary embodiment is employed for mammography, radiographic image data obtained by imaging the breast of a subject is stored in the storage section 46D.

When irradiated with radiation from the radiation source 31 of the radiation irradiation section 24 according to the exposure conditions, the radiation detector 42 detects the radiation and outputs image data expressing a radiographic image to the imaging apparatus control section 46. Details regarding the configuration of the radiation detector 42 are given later.

The imaging apparatus control section 46 is capable of communicating with the image processing apparatus 50 through the communication I/F section 48 and the network 56, and the imaging apparatus control section 46 performs transmission and reception of various data to and from the image processing apparatus 50. A management server 57 is also connected to the network 56. The management server 57 is configured including a storage section 57A that stores specific management data. The imaging apparatus control section 46 is enabled for communication with the management server 57 through the communication I/F section 48 and the network 56.

The image processing apparatus 50 is configured as a server computer and includes a display 52 that displays for example an operation menu and various data, and an operation input section 54 configured including plural keys for inputting various data and operation instructions. The image processing apparatus 50 includes a CPU 60 for controlling the apparatus operation overall, ROM 62 that is pre-stored with various programs including a control program, RAM 64 for temporary storage of various data, a HDD 66 for storing and retaining various data, a display driver 68 for controlling the display of various data on the display 52, an operation input detection section 70 for detecting operation states with respect to the operation input section 54, a communication I/F section 72 that is connected to the imaging apparatus 41 through the network 56 and that performs transmission and reception of various data to and from the imaging apparatus 41, and an image signal output section 74 that outputs image data through a display cable 58 to the display device 80. The image processing apparatus 50 acquires image data (digital data) expressing radiographic images stored in the storage section 46D from the imaging apparatus 41, via the communication I/F section 72.

The CPU 60, the ROM 62, the RAM 64, the HDD 66, the display driver 68, the operation input detection section 70, the communication I/F section 72 and the image signal output section 74 are mutually connected through a system BUS. The CPU 60 is accordingly able to access the ROM 62, the RAM 64 and the HDD 66. The CPU 60 is capable of performing various control, such as controlling display of various data on the display 52 through the display driver 68, controlling transmission and reception of various data to and from the imaging apparatus 41 through the communication I/F section 72, and controlling image display on a display section 80A of the display device 80 through the image signal output section 74. The CPU 60 is also capable of ascertaining user operation states to the operation input section 54 through the operation input detection section 70.

Figure 2:
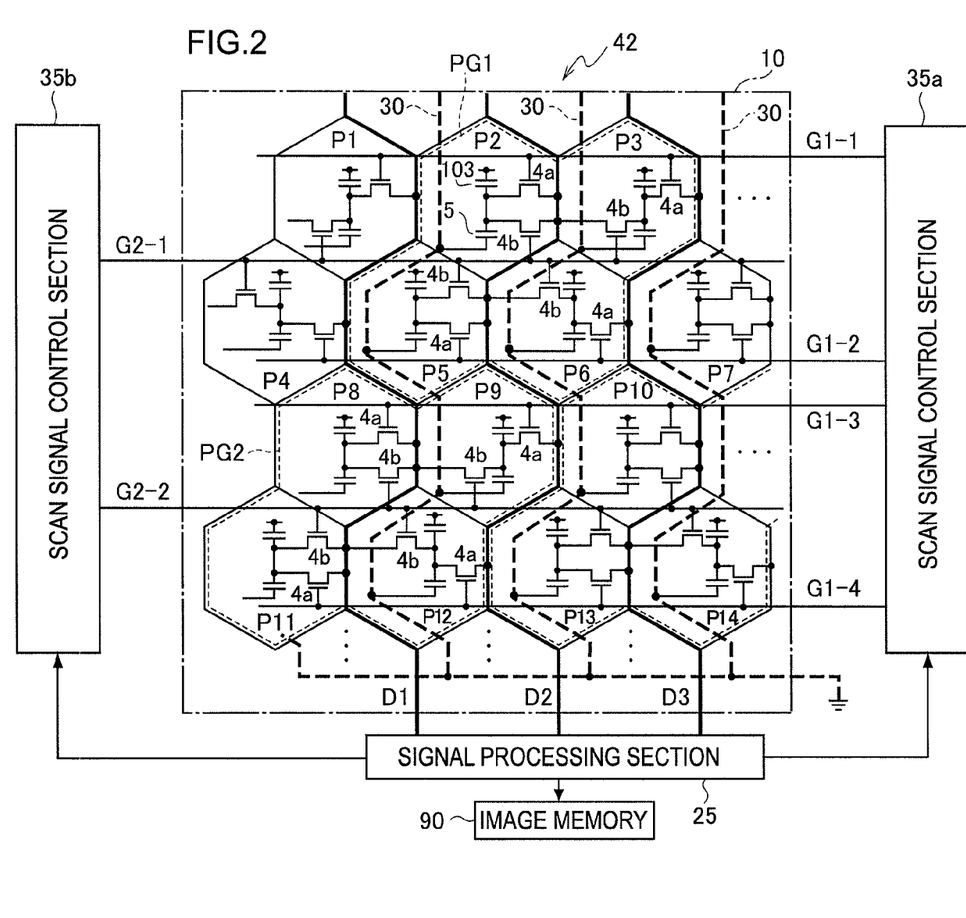
FIG. 2 is a drawing illustrating an electrical configuration of a radiation detector of an imaging apparatus according to the first exemplary embodiment.

FIG. 2 illustrates an electrical configuration of a radiation detector of an imaging apparatus according to the present exemplary embodiment. A radiation detection element 10 of the radiation detector 42 illustrated in FIG. 2 is configured with plural pixels 20 that have hexagonal shaped pixel regions arrayed adjacently in a two dimensional honeycomb pattern, so as to configure a region that is substantially rectangular shaped overall. Each of the pixels 20 is configured including a sensor portion 103 that receives radiation (X-rays) that has been irradiated and generates charges, a charge storage capacitor 5 that accumulates the charges that have been generated in the sensor portion 103, and two thin film transistors (also referred to as TFT switches) 4a, 4b for reading the charges accumulated in the charge storage capacitors 5.

Note that, disposing the pixels 20 in a honeycomb pattern means that the pixels 20 having hexagonal shaped pixel regions of the same size are arrayed in a first pixel row and pixels 20 having hexagonal shaped pixel regions of the same size as the first pixel row pixels 20 are arrayed in a second pixel row, and the first pixel row and the second pixel row are repeated along the column direction (the vertical direction in FIG. 2). The pixels 20 in the first pixel row are arrayed in a row direction (the horizontal direction in FIG. 2) such that one side of mutually adjacent pixels are in adjacent contact with each other. The pixels 20 in the second pixel row are arrayed in the row direction such that two adjoining sides of each of the second pixel row pixels 20 are respectively in adjacent contact with two neighboring sides from mutually adjacent pixels in the first pixel row. The pixels 20 of the second pixel rows are disposed aligned between adjacent pixels of the first pixel rows, such that the pixels 20 of the second pixel rows are displaced in the row direction from the pixels 20 in the first pixel rows by ½ the array pitch of the first pixel row pixels 20.

The radiation detector 42 includes first scan lines G1-1 to G1-4 (also referred to as first scan lines G1) that are connected to the gate terminals of the TFT switches 4a provided in each of the pixels 20, in order to perform ON/OFF control of the TFT switches 4a, second scan lines G2-1, G2-2 (also referred to as second scan lines G2) that are connected to the gate terminals of the TFT switches 4b in order to perform ON/OFF control of the TFT switches 4b, plural data lines D1 to D3 that read charges generated in the sensor portions 103 that have been accumulated in the charge storage capacitors 5 (also referred to as data lines D or as data lines 3), and common ground lines 30.

In FIG. 2, for ease of explanation and illustration, an example is shown of a configuration disposed with 4 first scan lines G1, 2 second scan lines G2, 3 data lines D, and 3 common ground lines 30. In general when, for example, there are m×n individual pixels 20 disposed in the row direction and the column direction (wherein m and n are positive integers), m of the first scan lines G1 and n of the data lines D are provided. In such cases, the number of second scan lines G2 is half the number of the first scan lines G1, namely m/2 lines are provided. As described later, the radiation detection element 10 of the radiation detector 42 employs a radiation-charge conversion material, such as amorphous selenium, that performs direct conversion of radiation into charges.

Note that each of the sensor portions 103 of the pixels 20 is connected to common lines, not shown in the drawings, in which a bias voltage is applied from a power source (not shown in the drawings) through the common lines.

In the radiation detector 42, the scan lines G1, G2 are disposed so as to intersect with the data lines D and the common ground lines 30. The data lines D are disposed along the peripheral edges of the hexagonal shaped pixels 20 in a zigzag pattern (so as to meander) so as to bypass these pixels 20. Namely, the data lines D extend in the column direction while running along 3 contiguous sides out of the peripheral edges (6 sides) of each of the individual pixels 20. The common ground lines 30 are also disposed in a zigzag pattern (so as to meaner) to keep away from the TFT switches 4a, 4b of each of the pixels 20.

The gate electrodes of the TFT switches 4a are connected to the first scan lines G1, and the gate electrodes of the TFT switches 4b are connected to the second scan lines G2. Either the drain electrodes or the source electrodes of the TFT switches 4a, 4b are connected to one of the electrodes of the charge storage capacitors 5, and the other out of the drain electrodes and the source electrodes are connected to the data lines D. When imaging a radiographic image with the radiation detector 42, during irradiation with external radiation (X-rays), OFF signals are output to the first scan lines G1 and each of the TFT switches 4a is switched OFF, and OFF signals are output to the second scan lines G2, switching each of the TFT switches 4b OFF. The charges generated in the sensor portions 103 are accordingly accumulated in each of the charge storage capacitors 5.

When reading an image, for example a still image, ON signals are output in sequence one line at a time to the first scan lines G1, switching the TFT switches 4a in each of the pixels 20 ON. Or, for example when reading a video image, ON signals are output in sequence one line at a time to the second scan lines G2, switching ON the TFT switches 4b of plural pixels in pixel groups (described later). The charges accumulated in each of the charge storage capacitors 5 are thereby read as electrical signals, and a radiographic image is obtained by converting the read electrical signals into digital data.

A signal processing section 25 includes signal detectors (not shown in the drawings) that detect charges flowing out of each of the data lines D1 to D3 as electrical signals, and subjects the detected electrical signals to specific processing. The signal processing section 25 also respectively outputs control signals expressing a signal detection timing and control signals expressing a scan signal output timing to the signal detectors and the scan signal control sections 35a, 35b. As a result, on receipt of the control signals from the signal processing section 25, the scan signal control section 35a outputs signals to the first scan lines G1-1 to G1-4 for switching the TFT switches 4a ON/OFF. The scan signal control section 35b also outputs signals to the second scan lines G2-1, G2-2 for switching the TFT switches 4b ON/OFF.

The charge signals transmitted by the individual data lines D1 to D3 are amplified in the signal processing section 25 by amplifiers, and are held in sample-and-hold circuits (not shown in the drawings). The charge signals held by the individual sample-and-hold circuits are input in sequence to a multiplexer (not shown in the drawings), and then converted into digital image data by an A/D converter. Note that an image memory 90 is connected to the signal processing section 25, and the digital image data output from the A/D converter is stored in sequence in the image memory 90. The image memory 90, for example, stores digital image data for plural frames worth of imaged radiographic images.

Figure 3:
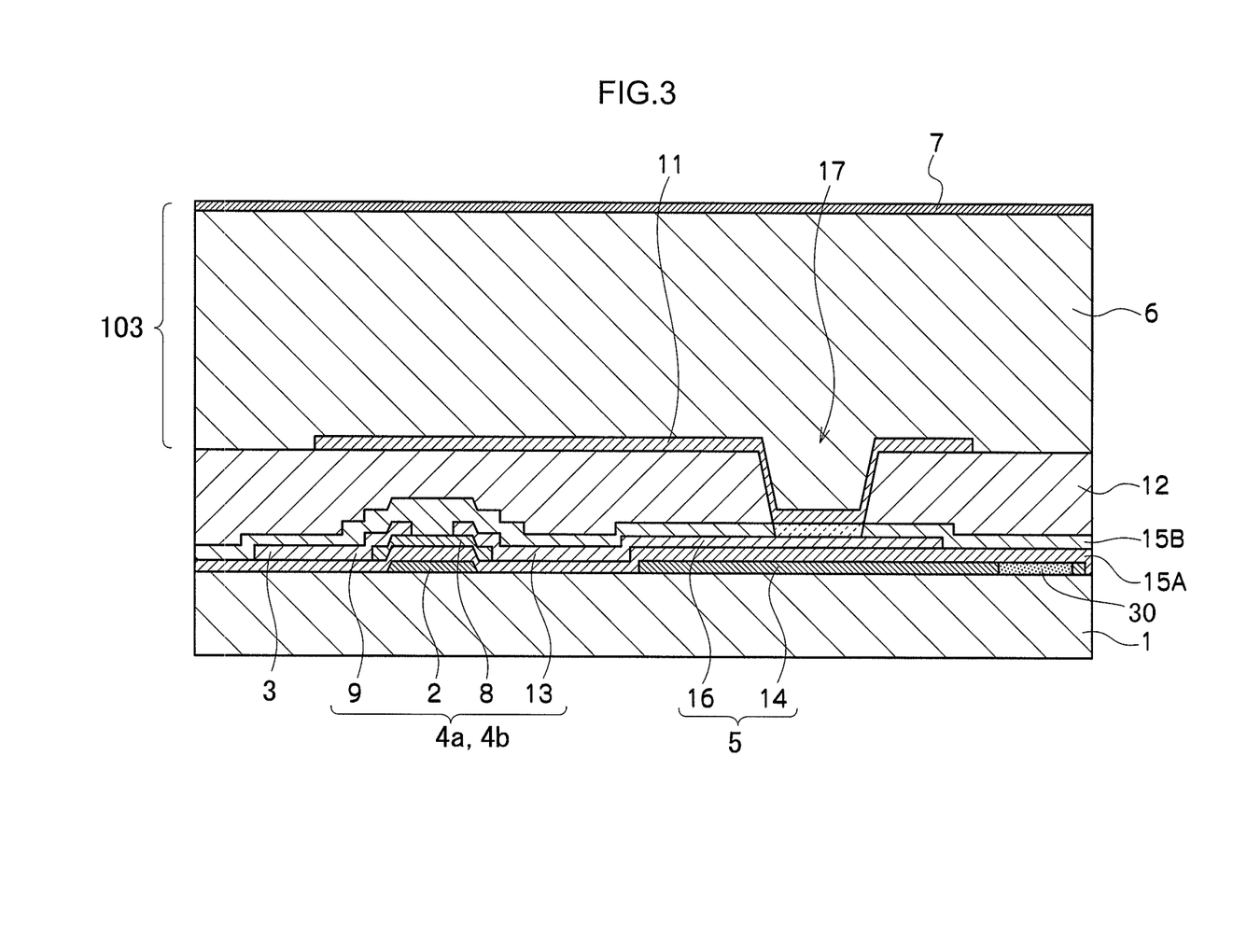
FIG. 3 is a drawing illustrating a partial cross-sectional view of a radiation detection element of a radiation detector according to the first exemplary embodiment.

FIG. 3 illustrates a partial cross-sectional view including a single pixel of a radiation detection element of a radiation detector according to the first exemplary embodiment. The radiation detection element 10 of the radiation detector 42 is, as shown in FIG. 3, a structure in which gate electrodes 2, scan lines 101 (not shown in FIG. 3) and storage capacitor lower electrodes 14 are formed as a gate wiring layer on an insulating substrate 1. A wiring layer (also referred to as a source wiring layer) formed with source electrodes 9, drain electrodes 13, signal lines 3, and storage capacitor upper electrodes 16 is formed using a layered film of, for example, Al or Cu, or mainly of Al or Cu. An impurity doped semiconductor layer (not shown in the drawings) such as impurity doped amorphous silicon is formed between semiconductor active layers 8 and the source electrodes 9, and the drain electrodes 13. Note that the source electrodes 9 and the drain electrodes 13 are reversed in the TFT switches 4a, 4b according to the polarity of the charges collected and accumulated by a lower electrode 11.

The gate wiring layer for the gate electrodes 2 is formed using a layered film of, for example, Al or Cu, or mainly of Al or Cu. An insulating film 15A is formed on one face on the gate wiring layer, and the locations of the insulating film 15A above the gate electrodes 2 act as gate insulation films for the TFT switches 4a, 4b. The insulating film 15A is, for example, configured from SiNx, and is formed, for example, by a Chemical Vapor Deposition (CVD) film forming process. The semiconductor active layers 8 are formed with island shapes on the insulation film 15A above each of the gate electrodes 2. The semiconductor active layers 8 are channel portions of the TFT switches 4a, 4b and are, for example, formed from an amorphous silicon film.

The source electrodes 9 and the drain electrodes 13 are formed in a layer above the gate electrodes 2. In the wiring layer in which the source electrodes 9 and the drain electrodes 13 are formed, the data lines 3 are also formed together with the source electrodes 9 and the drain electrodes 13. The storage capacitor upper electrodes 16 are also formed at positions on the insulating film 15A corresponding to the storage capacitor lower electrodes 14. The drain electrodes 13 are connected to the storage capacitor upper electrodes 16. The data lines 3 are disposed running along the peripheral edges of the pixels 20 in the manner described above, bent so as to bypass between one pixel and an adjacent pixel. The data lines 3 are connected to the source electrodes 9 formed to the pixels 20 in each of the pixel rows.

A TFT protection layer 15B is formed over substantially the whole surface (substantially all regions) of the region where the pixels are provided on the substrate 1 so as to cover the source wiring layer. The TFT protection layer 15B is formed, for example, from a material such as $SiN_x$ by, for example, a CVD film forming method. A coated interlayer insulating film 12 is then formed on the TFT protection layer 15B. The interlayer insulating film 12 is formed from a low permittivity (specific permittivity $\epsilon_r$=2 to 4) photosensitive organic material (examples of such materials include positive working photosensitive acrylic resin materials with a base polymer formed by copolymerizing methacrylic acid and glycidyl methacrylate, mixed with a naphthoquinone diazide positive working photosensitive agent) at a film thickness of 1 μm to 4 μm.

In the radiation detector 42 according to the present exemplary embodiment, inter-metal capacitance between metal disposed in the layers above the interlayer insulating film 12 and below the interlayer insulating film 12 is suppressed to be small by the interlayer insulating film 12. Generally the materials of the interlayer insulating film 12 also function as a flattening film, exhibiting an effect of flattening out steps in the layers below. In the radiation detection device 10 of the radiation detector 42, contact holes 17 are formed in the interlayer insulating film 12 and the TFT protection layer 15B at locations corresponding to the storage capacitor upper electrodes 16.

Lower electrodes 11 of each of the sensor portions 103 are formed on the interlayer insulating film 12 for each of the pixels 20, so as to cover the pixel region while also filling each of the contact holes 17. The lower electrodes 11 are formed from an amorphous transparent conducting oxide film (ITO) and are connected to the storage capacitor upper electrodes 16 through the contact holes 17. As a result, the lower electrodes 11 and the TFT switches 4a, 4b are electrically connected through the storage capacitor upper electrodes 16. Note that while the lower electrodes 11 are preferably formed in shapes to match the shapes of the pixel regions of the pixels 20, there is no limitation thereto. For example, when the pixel regions of the pixels 20 are regular hexagonal shaped, the lower electrodes 11 are preferably formed with slightly smaller regular hexagonal shapes so as not to touch the lower electrodes of adjacent pixels. Similarly, when the pixel regions of the pixels 20 are formed in flattened hexagonal shapes the lower electrodes 11 are preferably formed in slightly smaller hexagonal shapes. As long as the pixel placement of the lower electrodes configures a hexagonal lattice, configuration may be made with beveled corner hexagonal shaped or square shaped lower electrodes 11.

A photoelectric conversion layer 6 is uniformly formed on the lower electrodes 11 over substantially the entire surface of the pixel region where the pixels 20 are provided on the substrate 1. The photoelectric conversion layer 6 generates charges (electrons-holes) due to irradiation of radiation such as X-rays. In other words, the photoelectric conversion layer 6 has electrical conduction properties and is employed to convert image data from radiation into charge data. For example, the photoelectric conversion layer 6 may be formed from amorphous selenium (a-Se) having selenium as the main component and a film thickness of 100 μm to 1000 μm. Here, the main component means contained at a ratio of 50% of more. An upper electrode 7 is formed on the photoelectric conversion layer 6. The upper electrode 7 is connected to a bias power source (not shown in the drawings) and supplies a bias voltage (for example several kV) from the bias power source. The scan lines G1, G2, the data lines 3, the common ground lines 30 and the TFT switches 4a, 4b are disposed at a lower layer side of the sensor portions 103 configured by the photoelectric conversion layer 6.

In the radiation detection device of the radiation detector, the gate electrodes 2, the first and second scan lines G1, G2 and the storage capacitor lower electrodes 14 are formed as the gate wiring layer on the insulating substrate 1, and the common ground lines 30 are formed on the insulating substrate 1, for example in the same metal layer as the storage capacitor lower electrodes 14.

Explanation next follows regarding operation of the radiation detector 42 according to the present exemplary embodiment. Charges (electron-hole pairs) are generated in the photoelectric conversion layer 6 when X-rays are irradiated onto the photoelectric conversion layer 6 in a state in which a bias voltage is being applied across the upper electrode 7 and the storage capacitor lower electrodes 14. The photoelectric conversion layer 6 and the charge storage capacitors 5 are electrically connected in series, and so electrons generated in the photoelectric conversion layer 6 migrate to the + (plus) electrode side and holes migrate to the − (minus) electrode side.

During image detection, OFF signals (0V) are output from the scan signal control sections 35a, 35b to all the scan lines G1, G2, applying a negative bias to the gate electrodes of the TFT switches 4a, 4b. Each of the TFT switches 4a, 4b are thereby maintained in an OFF state. As a result, electrons generated in the photoelectric conversion layer 6 are collected by the lower electrodes 11, and accumulated in the charge storage capacitors 5. The photoelectric conversion layer 6 generates a charge amount according to the amount of radiation irradiated, and so, charges according to image data carried by the radiation are accumulated in the charge storage capacitors 5 of each of the pixels. Note that the charge storage capacitors 5 need to be given a larger capacitance than the capacitance formed by the photoelectric conversion layer 6 due to the voltage of several kV referred to above being applied across the upper electrode 7 and the storage capacitor lower electrodes 14.

During image reading, the radiation detector 42 performs in a still imaging mode or a video imaging mode according to instruction from the image processing apparatus 50 as described above. When instruction was for the still imaging mode, the signal processing section 25 controls the scan signal control section 35b such that gate control signals are output from the second scan lines G2-1, G2-2 for switching the TFT switches 4b in each of the pixels 20 OFF. The signal processing section 25 also controls the scan signal control section 35a to apply ON signals for example with a voltage of +10 to 20V in sequence from the first scan lines G1-1 to G1-4 to the gates of each of the TFT switches 4a in order to switch the TFT switches 4a in each of the pixels 20 ON. The TFT switches 4a in each of the pixels 20 are thereby switched to an ON state in sequence for each of the pixel rows, charges are read from the sensor portions 103 by the TFT switches 4a, and signals corresponding to these charges are output to the data lines D.

Thus in the radiation detector 42, in the still imaging mode, in all of the data lines D1 to D3, charge signals flow corresponding to each of the pixels 20 in each of the pixel rows. Accordingly, image data expressing an image representing radiation irradiated onto the radiation detection element 10 of the radiation detector 42 can be obtained. Then, in the signal processing section 25, the charge signals are converted into digital signals, and a radiographic image based on the image data corresponding to the charge signals is generated.

Explanation follows regarding the video imaging mode. In the radiation detector 42 according to the present exemplary embodiment, out of the plural pixels 20 shown in FIG. 2, the gate terminals of each of the TFT switches 4b in the four pixels P2, P3, P5, P6 surrounded by the dashed line, for example, are connected to the second scan line G2-1. Similarly, the gate terminals of each of the TFT switches 4b in the four pixels P8, P9, P11, P12 surrounded by the dashed line are connected to the second scan line G2-2. The pixels P2, P3, P5, P6 are collectively referred to here as pixel group PG1, and the pixels P8, P9, P11, P12 are collectively referred to as pixel group PG2. Note that, while simplified in FIG. 2, the pixel groups in the radiation detection element 10 also configure plural other pixel groups of four specific pixels other than the pixel groups PG1, PG2 (see for example FIG. 4).

When the video imaging mode is instructed to the radiation detector 42, the signal processing section 25 controls the scan signal control section 35a so as to switch the TFT switches 4a of each of the pixels 20 OFF, and outputs OFF signals from the first scan lines G1-1 to G1-4 to each of the gate electrodes of the TFT switches 4a of each of the pixels 20.

The signal processing section 25 also controls the scan signal control section 35b to output scan signals (ON signals)

in sequence using the second scan lines G2-1, G2-2. Namely, when an ON signal is output by the second scan line G2-1, the TFT switches 4b of the four individual pixels P2, P3, P5, P6 of the pixel group PG1 are switched ON. As a result, a charge signal, that is the sum of the charges that have been accumulated in each of the charge storage capacitors 5 of the four individual pixels P2, P3, P5, P6, is output to the data line D2. When an ON signal is then output from the second scan line G2-2, the TFT switches 4b of the four individual pixels P8, P9, P11, P12 are switched ON. In such cases, a charge signal, that is the sum of the charges that have accumulated in each of the charge storage capacitors 5 of the four individual pixels P8, P9, P11, P12, is output to the data line D1.

Note that, although simplified in FIG. 2, when ON signals are output by the second scan lines G2-1, G2-2, subsequent plural other pixels along the row directions of the pixels of the pixel groups PG1, PG2 also output charge signals that are summed in four pixel units to data lines, similarly to with the pixel groups PG1, PG2.

When in the video imaging mode, in the plural pixel groups configured by bundles of four pre-specified pixels from the plural pixels configuring the radiation detection element 10, the charges accumulated in the four individual pixels are combined (called binning) and a charge signal corresponding to the binned charges is output to the data lines. This means that when performing video imaging, charge signals each corresponding to the sum of charges of 2 pixels×2 pixels flow alternately in adjacent data lines D (alternately in the even numbered data lines and the odd numbered data lines in FIG. 2).

Figure 4:
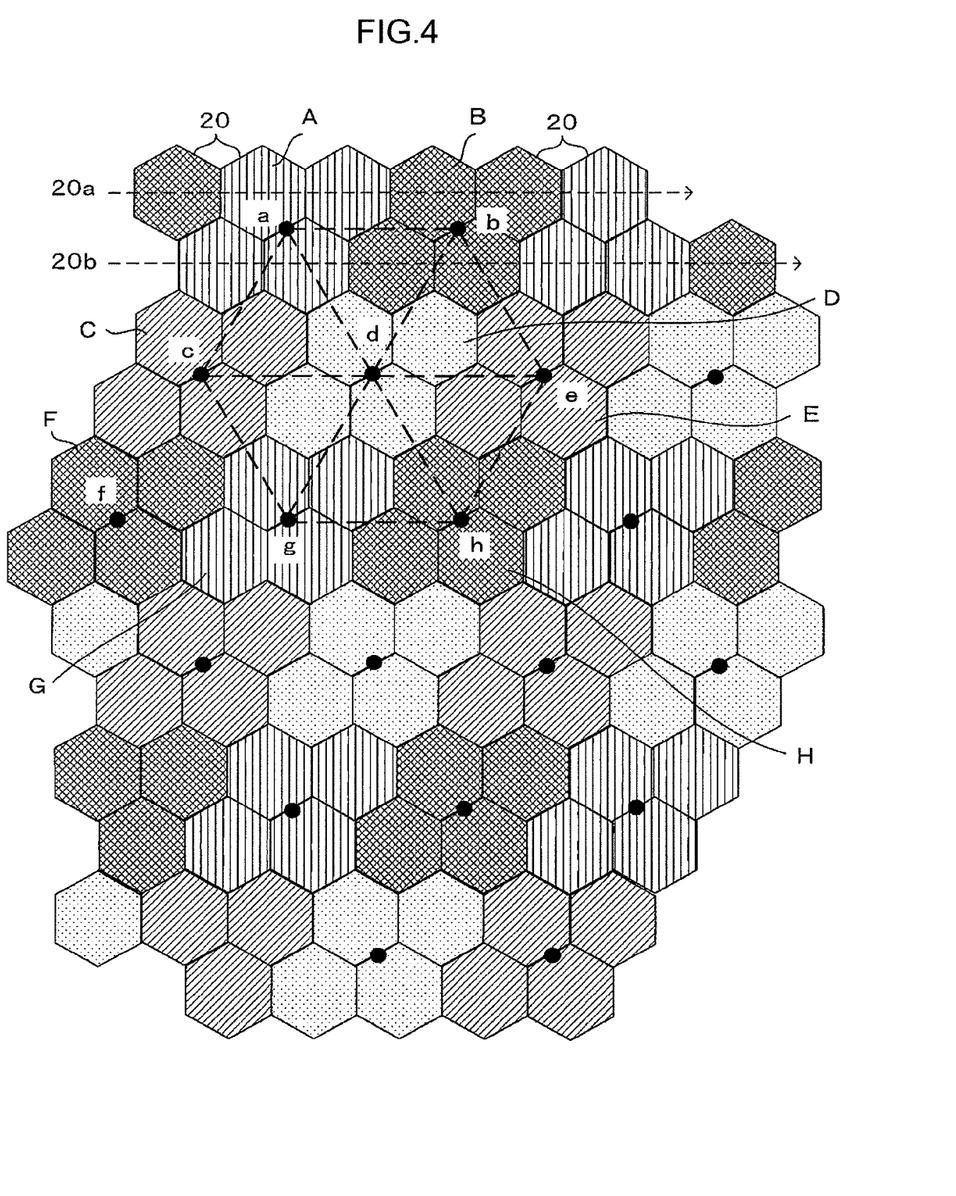
FIG. 4 is a drawing illustrating a layout of pixels and pixel groups subject to binning.

FIG. 4 illustrates a layout of pixels and pixel groups subject to binning in the video imaging mode described above. Note that, in FIG. 4, a pattern of shading has been added to each of the pixels in adjacent pixel groups to make it easier to distinguish the respective pixel groups.

In the example illustrated in FIG. 4, the radiation detection element 10 of the radiation detector 42 features pixel groups A, B, C, D, E, F, G, H formed from 4 adjacent pixels as described above. For example, the pixel group A is formed from a total of 4 pixels (the 4 pixels shaded with vertical lines), these being 2 adjacent pixels out of pixels 20 in a first pixel row in the row direction indicated with the label 20a in FIG. 4, and 2 mutually adjacent pixels out of the pixels 20 in a second pixel row in the row direction indicated with the label 20b in FIG. 4 that are positioned below the first pixel row and shifted by ½ the array pitch with respect to the 2 pixels in the first pixel row.

In other words, each of the pixel groups can be defined as being a combination of 4 pixels configured by 3 pixels, disposed such that two adjoining sides of each of the pixels are respectively mutually adjacent to one side of the remaining 2 pixels, and by 1 pixel, disposed such that two adjoining sides are respectively mutually adjacent to one side of 2 pixels out of the 3 pixels. The combination of 4 pixels may also be described as being a combination of 4 pixels formed from 2 pairs of mutually adjacent pixels disposed alongside each other, with 2 adjoining sides of 1 pixel from a first pair disposed mutually adjacent to 1 side of each of the 2 pixels in the other pair respectively.

When still imaging mode is instructed as described above, in the radiation detector 42 of the present exemplary embodiment, the signal processing section 25 switches the TFT switches 4a in each of the pixels 20 of the radiation detector 42 ON, reads the charges from each of the pixels, and outputs signals corresponding to the charges to the data lines D. Since hexagonal shaped pixels are employed as the individual pixels in the radiation detection element 10 of the radiation detector 42 a high resolution may be secured in each of the horizontal, vertical and diagonal directions.

However, in the video imaging mode, due to the signal processing section 25 switching the TFT switches 4b inside 4 pixels configuring each of the pixel groups ON as described above, the 4 pixels act as a single pixel, and binning is performed to combine 4 pixels worth of charges. The positions of the center of gravity for each of the pixel groups A, B, C, D, E, F, G, H formed from 4 pixels are positioned at the black dots indicated respectively as a, b, c, d, e, f, g, h.

In the example indicated in FIG. 4, when performing 4 pixel binning for each of the pixel groups, a regular hexagonal shape is formed by connecting the centers of gravity a-c-g-h-e-b-a, with the center of gravity d of the pixel group D at the center. It can also be seen that the inter center of gravity distances of these pixel groups in the 6 directions d to a, d to c, d to g, d to h, d to e, and d to b are all the same as each other. Thus by making each of the pixels 20 a hexagonal shape, even resolution may be secured in each of the horizontal, vertical and diagonal directions before binning. Moreover, since a regular hexagonal shape is also formed by connecting together the centers of gravity of the pixel groups, even resolution may also be secured in each of the horizontal, vertical and diagonal directions after binning.

Namely, by employing the center of gravity a, b, c, d, e, f, g, h of each of the regions surrounded by the outlines of the pixel groups A, B, C, D, E, F, G, H, plural adjacent individual regions are formed with 1 center of gravity d at the inside, and hexagonal shaped regions formed by the line segments connecting the 6 individual centers of gravity a, c, g, h, e, b present at the periphery of the center of gravity d. The combinations of each of the pixels in each of the pixel groups are determined such that the plural individual hexagonal shaped regions thus formed are arrayed in a honeycomb pattern. Accordingly, unevenness in each of the horizontal, vertical and diagonal directions of the pixel positions (the center of gravity positions of the pixel groups) after binning may be suppressed, and even resolution may be secured in each of the respective directions, similarly to in an image before binning.

Since the centers of gravity arrayed before binning, and the hexagonal shaped regions formed by the centers of gravity arrayed after binning, both are arrayed in a honeycomb pattern, processing may be performed with a similar algorithm when performing pixel density conversion after binning to when performing pixel density conversion without binning Namely, the algorithm for pixel density conversion processing may be commonly employed both before and after binning, without preparing another separate algorithm for pixel density conversion processing after binning. In the image processing apparatus 50 a program for performing pixel density conversion on image data expressing radiographic images detected by the radiation detector 42 is stored on the ROM 62 and/or the HDD 66. The image data output to the display device 80 is accordingly image data after performing pixel density conversion.

Figure 5:
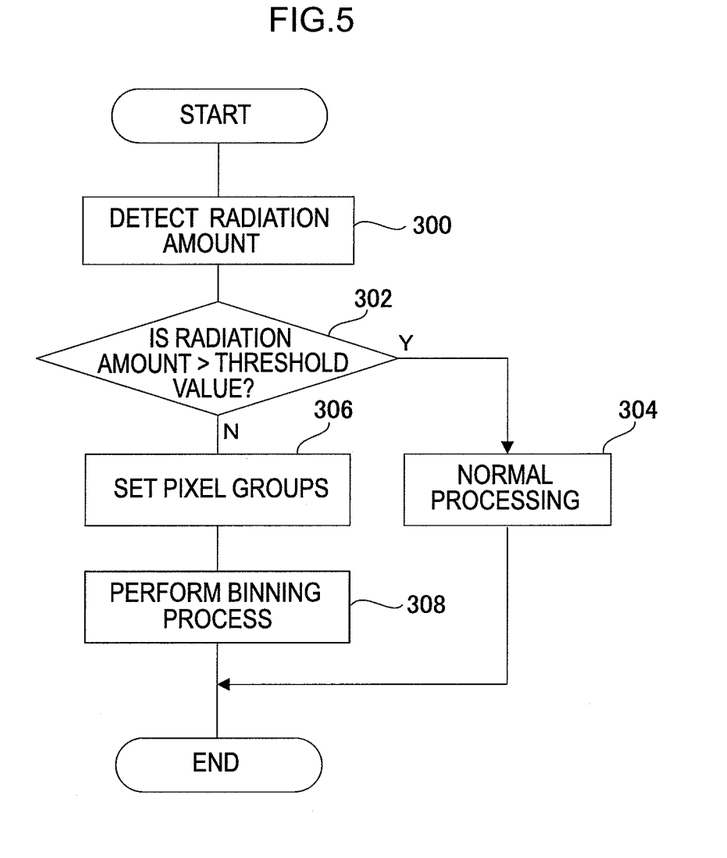
FIG. 5 is a flow chart showing an example of an imaging processing sequence of a radiographic imaging system according an exemplary embodiment.

FIG. 5 is a flow chart showing an example of an imaging process sequence executed in the image processing apparatus 50 of a radiographic imaging system according to the present exemplary embodiment. At step 300 of FIG. 5, the amount of radiation irradiated from the radiation irradiation section 24 is detected in the radiation detector 42 of the imaging apparatus 41. Then at step 302, determination is made as to whether or not the radiation amount has exceeded a predetermined threshold value. It is determined that sufficient sensitively can be obtained for imaging (image S/N will be sufficient) when determined that the amount of radiation irradiated has exceeded the threshold value. Processing then proceeds to step 304 where control signals are transmitted to the respective plural pixels 20 and normal processing to read the signals of the charges individually accumulated in the storage capacitors is performed (still imaging mode).

However, when determined at step 302 that the amount of radiation irradiated is the threshold value or lower, it is considered that the S/N for the image obtained would be insufficient, processing proceeds to step 306 and processing is performed to image a high S/N image. Specifically, the pixel groups A, B, C, D, E etc. formed from specific 4 pixels are set as described above. At step 308, scan signals (ON signals) are output by the scan signal control section 35b to the second scan lines G2 to switch on the TFT switches 4b of each of the pixels disposed in the pixel groups A, B, C, D, E etc., and binning processing is performed to treat the 4 pixels of each of the pixel groups as a single pixel. Thus, if the amount of radiation irradiated is the threshold value or lower, a radiographic image with good S/N is obtained by processing to combine the charges of plural pixels (binning) due to the consideration that otherwise there would be insufficient imaging sensitivity.

Note that, in the imaging process shown in FIG. 5, process is performed in consideration of the S/N of the radiographic image that will be obtained according to the amount of radiation irradiated. However there is no limitation thereto. For example, configuration may be made so as to switch between normal processing without binning and processing with binning according to instruction for the still imaging mode or the video imaging mode, irrespective of the amount of radiation irradiated. Configuration may be made to perform the above switching according to the required resolution for imaging.

In the present exemplary embodiment, binning is performed by simultaneously reading and combining 4 pixels worth of charges in the radiation detection element of the radiation detector for plural predetermined pixel groups, each configured from 4 respective pixels out of plural hexagonal shaped pixels arrayed on the radiation detector in a honeycomb pattern. Accordingly, the S/N may be raised by increasing the amount of charge collected, and may enable application to a video imaging mode demanding a high frame rate as well as application to low sensitivity images generated by irradiating a small amount of radiation.

Moreover, combination of each of the pixels in each of the pixel groups is determined such that plural hexagonal shaped regions are arrayed in a honeycomb pattern. Each of the plural hexagonal shaped regions are formed by including inside 1 center of gravity of the region surrounded by the outlines of the pixel groups and the line segments connecting the 6 individual centers of gravity present at the periphery of the 1 center of gravity. Accordingly, unevenness of the pixel positions (the center of gravity position when plural pixels are treated a single pixel clump) after binning in each of the horizontal, vertical and diagonal directions may be suppressed, and even resolution may be secured in each of the respective directions, similarly to in an image before binning. As a result, a common integrated circuit (IC) may be employed for pixel density conversion before and after binning.

When imaging a video image, charges are read with pixel groups configured from 2 pixels×2 pixels treated as single pixels, and binning process is performed to combine the charges accumulated in each of the pixels configuring the pixel groups. Accordingly, although the resolution is lower than that in a still image, the frame rate for reading charges from each pixel row may be made twice to that of a still imaging mode (the frame period may be halved). In comparison to the number of rows when scan lines are provided for each of the pixel rows subject to binning, the number of scan lines may also be reduced, to ½ the number of rows of pixels subjected to binning. In other words, in the configuration of the radiation detector illustrated in FIG. 2, in comparison to the 4 scan lines required when binning is not performed, the total number of scan lines required for scanning the pixels, including performing scanning with binning, has previously been twice the 4 lines, i.e. 8 lines. However, in the present exemplary embodiment only 1.5 times the 4 lines, i.e. 6 lines, are required.

Second Exemplary Embodiment

Explanation follows regarding a second exemplary embodiment of the present invention. A radiographic imaging system according to the second exemplary embodiment is configured similarly to the radiographic imaging system according to the first exemplary embodiment described above, and so further explanation thereof is omitted.

Figure 6:
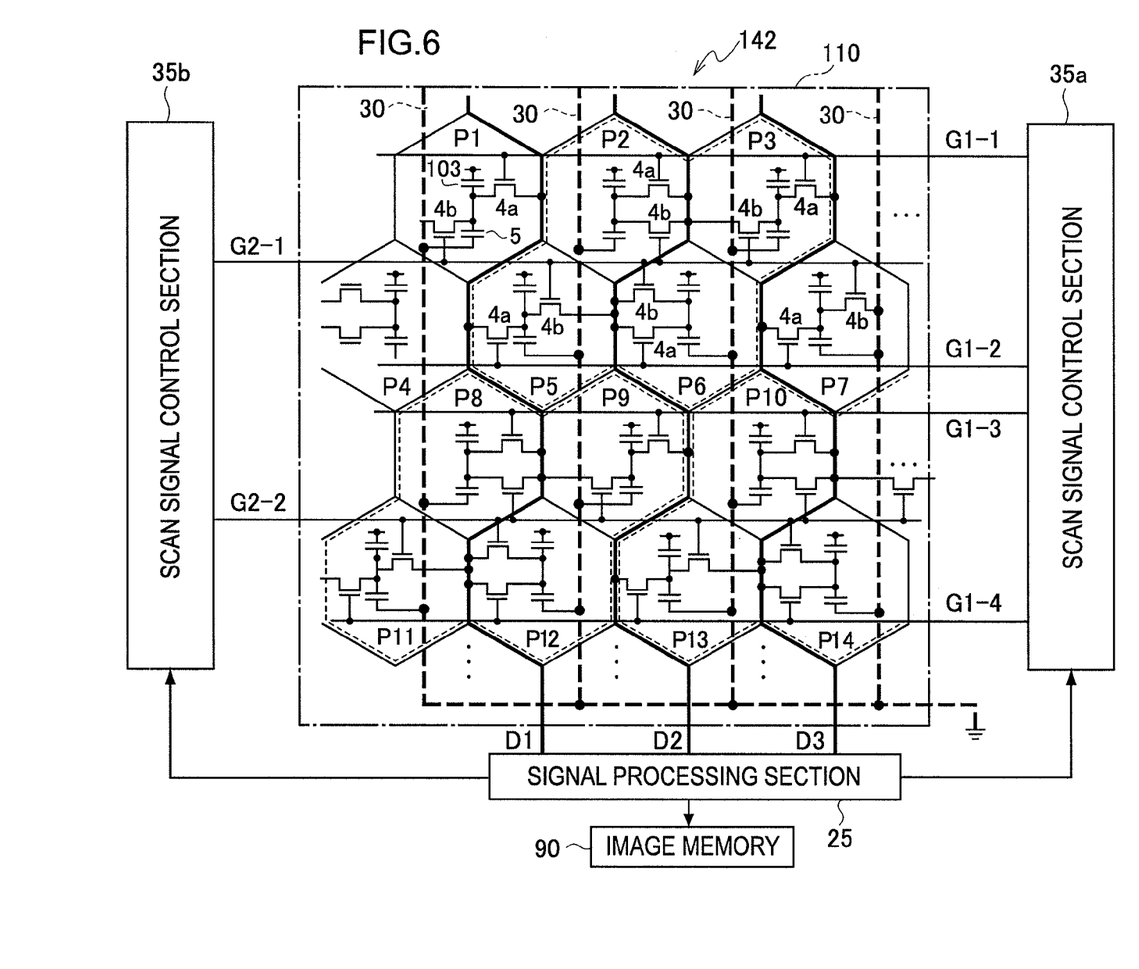
FIG. 6 is a drawing illustrating an electrical configuration of a radiation detector of an imaging apparatus according to a second exemplary embodiment of the present invention.

FIG. 6 illustrates an electrical configuration of a radiation detector of an imaging apparatus according to a second exemplary embodiment. A radiation detection element 110 of a radiation detector 142 illustrated in FIG. 6 is (similarly to the radiation detector according to the first exemplary embodiment illustrated in FIG. 2) configured with plural hexagonal shaped pixels 20 arrayed adjacent to each other in a two dimensional pattern, with the pixels 20 arrayed in a honeycomb pattern over a rectangular shaped pixel region. Similar configuration elements in the radiation detector 142 illustrated in FIG. 6 to those of the radiation detector according to the first exemplary embodiment illustrated in FIG. 2 are allocated the same reference numerals and further explanation is omitted.

As described above, radiation detectors include direct-conversion-type radiation detector that employ a radiation-charge conversion material, such as amorphous selenium, in a photoelectric conversion layer that absorbs radiation and converts the radiation to charges. Further, radiation detectors include indirect-conversion-type radiation detector provided with a scintillator that converts irradiated radiation into visible light and are configured containing an organic photoelectric conversion material that generates charges by receiving the light generated in the scintillator. The indirect-conversion-type radiation detectors are not provided with charge storage capacitors for accumulating charges obtained by photoelectric conversion, and so, common ground lines like those of direct conversion type radiation detectors are not required.

Therefore, in the indirect-conversion-type radiation detectors, bias lines for applying a common voltage to light detection elements are normally lines in an upper portion of photoelectric conversion sections, thereby securing a certain degree of freedom for bias line design. However, in direct-conversion-type radiation detectors, the charge storage capacitors referred to above are required, and so the bias lines need to be brought to the lower side of stacked layers. When selenium (Se) is employed in the photoelectric conversion layer for absorbing radiation and converting to charges, there are demands for high definition enhanced image quality, since the pixel size makes a direct contribution to raising resolution.

In radiation detectors, when, for example, common ground lines are meandered to match data lines, there is the possibility of various issues such as, for example, locations where the separation between TFT switches 4a, 4b in the pixels 20 is narrow occurring at portions meandering to the left or right, common ground lines and TFT switches colliding, and/or the capacity between data lines and the common ground line increasing.

The radiation detector 142 of the imaging apparatus according to the second exemplary embodiment is, as shown in FIG. 6, disposed with plural scan lines G1-1 to G1-4, G2-1, G2-2 running along a row direction (the horizontal direction in FIG. 6) arrayed parallel to each other, and plural data lines D1 to D3 disposed extending along a column direction (the vertical direction in FIG. 6) so as to intersect with the scan lines and to bend around along the peripheral edges of pixels 20. TFT switches 4a, 4b are disposed in each of the pixels 20 offset so as to enable specific free spaces to be secured in each of the pixels, and plural common ground lines 30 are disposed so as to pass through these free spaces.

As shown in FIG. 6, in the radiation detector 142, elements such as the TFT switches 4a, 4b and the charge storage capacitors 5 are disposed in each of the pixels 20, however the configuration varies by pixel row. Namely, the TFT switches 4a, 4b are disposed on the right hand side of the common ground lines 30 for the pixels P1, P2, P3 and so on, and then the TFT switches 4a, 4b are disposed on the left hand side of the common ground lines 30 for the pixels P5, P6, P7 and so on. This layout is repeated for subsequent pixel rows.

Note that in order to secure additional free spaces within pixels in each pixel row, the TFT switches 4a, 4b may be disposed in a region surrounded by a line segment dividing each of the pixels in two along the vertical direction, and surrounded by 3 adjoining sides out of the peripheral edges of each of the pixels where the data lines D are disposed. For example, in the pixels P1, P2, P3 etc., the TFT switches 4a, 4b are disposed in the region to the right hand side of the line segment that divides each of the pixels in two along the vertical direction, and in the pixels P5, P6, P7 etc. (the pixels in the pixel row positioned in the column direction below the pixels P1, P2, P3 etc.) the TFT switches 4a, 4b are disposed in the region to the left hand side of the line segment that divides each of the pixels in two along the vertical direction.

In the radiation detector 142, by disposing the TFT switches 4a, 4b in the pixels as described above, the need to bend the common ground lines 30 to avoid the contact points between the TFT switches 4a, 4b and the data lines D is eliminated. The plural common ground lines 30 can hence be disposed in a straight line shape between the plural data lines D1 to D3 while intersecting with the scan lines, without the common ground lines 30 intersecting with the data lines D1 to D3. As a result, the present exemplary embodiment may avoid the raise the resistance of the common ground lines, minimize the connecting lines between storage capacitor lower electrodes 14, and the ground lines and the storage capacitor lower electrodes 14 may be maintained at a constant voltage (for example ground voltage) by efficiently reducing contact resistance and line resistance. Note that reference here to disposing the common ground lines 30 in a straight line shape means that a straight line shape is maintained within a range obtainable allowing for processing error in manufacturing the radiation detector 142.

Operation for imaging radiographic images with the radiation detector 142 according to the second exemplary embodiment is similar to that of the radiation detector 42 according to the first exemplary embodiment described above. Namely, when in still imaging mode, signals are output from the scan signal control section 35a to the first scan lines G1-1 to G1-4 to switch the TFT switches 4a inside each of the pixels 20 ON, and signals are output from the scan signal control section 35b to the second scan lines G2-1, G2-2 to switch the TFT switches 4b in each of the pixels 20 OFF. Charge is read out from the sensor portions 103 of each of the pixels 20, and the signals corresponding to the charges are output to the data lines D1 to D3. Then using the charge signals corresponding to each of the pixels 20, image data is obtained expressing an image indicating the radiation irradiated onto the radiation detector 42.

When in the video imaging mode, similarly to the radiation detector 42 according to the first exemplary embodiment described above, signals are output to the first scan lines G1-1 to G1-4 to switch the TFT switches 4a in the pixels 20 OFF, and signals are output to the second scan lines G2-1, G2-2 to switch the TFT switches 4b in each of the pixels 20 ON. As a result, charges accumulated in 4 pixels are summed (binning is performed) for plural respective pixel groups (for example the pixels P2, P3, P5, P6 and the pixels P8, P9, P11, P12 surrounded by the dotted lines in FIG. 6) configured from predetermined 4 pixels out of the plural pixels configuring the radiation detection element 110. Charge signals corresponding to the binned charges are output to the data lines. Namely, charge signals of charges summed in 4-pixel units in the radiation detector 142 are output to the data lines.

As explained above, in the second exemplary embodiment, similarly to in the first exemplary embodiment described above, since even resolution can be secured in 6 directions (namely the horizontal, vertical and diagonal directions of the pixels) both before and after binning processing for plural pixel groups, the same common IC may be employed in pixel density conversion. Further, in the present exemplary embodiment, number of scan lines may also be reduced to ½ the number of pixel rows subjected to binning.

Moreover, due to arraying the common ground lines below the pixel electrodes in substantially straight line shapes, the storage capacitor lower electrodes of the charge storage capacitors of each of the pixels can be mutually connected together by the shortest common ground lines in a direct-conversion-type radiographic detector. Further, the need to make the common ground lines meander to match the data lines is also eliminated. Furthermore, in the present exemplary embodiments, since there is also no intersection of the data lines and the common ground lines, an increase in noise caused by such effects as induction in the data lines, and an increase in the interline capacitance between the data lines and the common ground lines, may also be avoided.

Further, in the present exemplary embodiments, the resolution of the radiation detection element may be raised without the common ground lines impeding higher definition of pixels of the radiation detection element. Moreover, in the manufacturing processes for the radiation detection element, the problem of a drop in manufacturing yield of the radiation detection element may be avoided due to making the line pitch between the data lines and the common ground lines narrower.

In the above exemplary embodiments, the hexagonal shaped pixels of the radiation detection element may include regular hexagonal shaped pixels and substantially hexagonal shaped pixel that have their corners beveled. Moreover, for example, flattened hexagonal shaped pixels squashed in the top-bottom direction on FIG. 2, and hexagonal shaped pixels when viewed in plan view may also be included. Namely, configuration may be made with hexagonal shaped pixels formed flattened such that one diagonal line out of 3 diagonal lines passing through the center of each of the pixels is shorter than the other two diagonal lines and the other two diagonal lines are of equal length to each other. Thus even though pixels of flattened hexagonal shape are employed, the relationships of the center of gravity separations and the six horizontal, vertical and diagonal directions may be maintained in before and after binning process.

In each of the above exemplary embodiments, explanation has been given of cases in which the present invention is applied to a direct-conversion-type radiation detector employing a radiation—charge conversion material such as amorphous selenium in a photoelectric conversion layer that absorbs radiation and converts the radiation into charge. However, the present invention is not limited thereto. For example, the present invention may be applied to an indirect-conversion-type radiation detector equipped with a scintillator that converts irradiated radiation into visible light.

In each of the above exemplary embodiments, a case in which the common ground lines 30 are disposed on the insulating substrate 1, have been disclosed. However, there is no limitation thereto. For example, the common ground lines 30 may be disposed in any layer below the lower electrodes 11 as the pixel electrode that collect charges generated in the photoelectric conversion layer 6. In such case, the common ground lines 30 lowering the irradiation efficiency of radiation irradiated onto the sensor portions 103 may be prevented.

In the above exemplary embodiments, as shown in for example FIG. 2, examples have been given of cases in which the scan signal control sections 35*a*, 35*b* are respectively disposed along the column direction to the sides of the radiation detection element 10 of the radiation detector 42. However, placement of the scan signal control sections are not limited thereto. For example, in mammography applications, the scan signal control sections 35*a*, 35*b* may be provided along the column direction at one side of the radiation detection element 10, 110, with the other side along the column direction configuring the chest wall side of the subject. In such cases, two general purpose gate ICs may be employed in a layered structure (double-layer) with the scan lines G1, G2 extending respectively therefrom, or the scan lines G1, G2 may extend from single custom gate IC.

In addition, the configurations, operations and the like of the radiation imaging system 100, the radiation detector 10, the pixels 20 and the like that were described in the present exemplary embodiment are examples, and may, of course, be changed in accordance with the situation within a range that does not deviate from the gist of the present invention.

Further, in the present exemplary embodiment, the radiation of the present invention is not particularly limited, and X-rays, y-rays or the like can be used.

What is claimed is:

1. A radiographic image detector comprising:
    a detection section including a plurality of pixels having hexagonal shaped pixel regions arrayed in a honeycomb pattern, each pixel including,
        a sensor portion that generates charges according to irradiated radiation,
        a first switching element that reads out the generated charges, and
        a second switching element that reads out the generated charges;
    a plurality of first scan lines that are disposed one for each of respective pixel rows of the plurality of pixels along an arrayed direction of the plurality of pixels, and that are each connected to a control terminal of the first switching elements in the corresponding pixel row;
    a plurality of second scan lines that are disposed one for each of respective pairs of column direction adjacent pixel rows from the plurality of pixel rows, and that are each connected to a control terminal of the second switching elements in the corresponding column direction adjacent pair of pixel rows; and
    a plurality of data lines that are disposed to respectively intersect with the plurality of first scan lines and the plurality of second scan lines, that transmit first charge signals corresponding to charges read out by the first switching elements in the plurality of pixels in response to signals output to the plurality of first scan lines, and that transmit second charge signals corresponding to a combined charge amount of 4 mutually adjacent pixels in a column direction adjacent pair of pixel rows read out by the second switching elements of the 4 mutually adjacent pixels in response to signals output to the plurality of second scan lines,
    wherein the 4 pixels configure a pixel group of repeating units of 2 successive pixels along the same pixel row direction, and 2 successive pixels along the pixel row direction of a pixel column direction adjacent pixel row to the first 2 pixels, and the 4 pixels are configured by 3 pixels disposed such that two adjoining sides of each of the pixels are respectively mutually adjacent to one side of the remaining 2 pixels, and by 1 pixel disposed such that two adjoining sides are respectively mutually adjacent to one side of 2 pixels out of the 3 pixels, and
    wherein combinations of the 4 pixels configuring respective pixel groups in the plurality of pixel groups are determined such that, when a plurality of hexagonal shaped regions are formed adjacent to each other, the plurality of hexagonal shape regions results in a honeycomb pattern array, and wherein each of the hexagonal shape regions are formed by including inside one center of gravity of a region surrounded by an outline of the plurality of pixel groups configured by the respective 4 pixels, and by connecting together 6 individual centers of gravity present at a periphery of the one center of gravity.

2. The radiographic image detector of claim 1, wherein the hexagonal shaped pixel regions are each formed in a regular hexagonal shape.

3. The radiographic image detector of claim 1, wherein the hexagonal shaped pixel regions are each formed in a flattened hexagonal shape.

4. The radiographic image detector of claim 3, wherein the hexagonal shaped pixel regions are formed flattened such that one diagonal line out of 3 diagonal lines passing through the center of each of the pixel regions is shorter than the other two diagonal lines, and the other two diagonal lines are of equal length to each other.

5. The radiographic image detector of claim 1, wherein the plurality of data lines are disposed bent along one portion of the hexagonal shaped pixel region periphery.

6. The radiographic image detector of claim 1,
    wherein the sensor portions includes a semiconductor film that receives irradiation of radiation and generates charges,
    wherein the charges are accumulated in a storage capacitor provided in each of the plurality of hexagonal shaped pixels, and
    wherein the charges accumulated in the storage capacitor are read by the first switching element and the second switching element.

7. The radiographic image detector of claim 6, further comprising: a plurality of common lines that connect together one electrode of each of the storage capacitors and that fixes the electrodes to a specific electrical potential.

8. The radiographic image detector of claim 7 wherein the sensor portions, the first switching elements and the second switching elements are disposed inside respective regions surrounded by a line segment dividing each of the pixels into two along a direction intersecting with the plurality of first scan lines extension direction and the plurality of second scan lines extension direction, and surrounded by three sides at the periphery of each of the pixels where the data lines are provided, and the plurality of common lines are disposed between the plurality of data lines without intersecting with the plurality of data lines.

9. The radiographic image detector of claim 8, wherein the plurality of common lines extend between the plurality of data lines in a straight line shape or in a substantially straight line shape.

10. The radiographic image detector of claim 9, wherein the plurality of common lines are connected to the plurality of data lines through the storage capacitors, the first switching elements and the second switching elements.

11. The radiographic image detector of claim 10, wherein the plurality of first scan lines, the plurality of second scan lines, the plurality of data lines, the plurality of common lines, the first switching elements and the second switching elements are disposed at a lower layer side of the sensor portions.

12. The radiographic image detector of claim 1, wherein the sensor portions includes a scintillator that converts the radiation that has been irradiated into visible light, and wherein, after the converted visible light has been converted into charges by a semiconductor layer, the charges are read by the first switching element and the second switching element.

13. A radiographic imaging apparatus comprising the radiographic image detector of claim 1, and that images a radiographic image with the radiographic image detector.

14. A radiographic imaging system comprising:
the radiographic imaging apparatus of claim 13; and
a control section that instructs the radiographic imaging apparatus to perform imaging of a radiographic image and acquires a radiographic image from the radiographic imaging apparatus,
wherein the control section comprises, a switching section that, based on an external instruction, switches between first image acquisition that acquires image data in single-pixel units of a radiographic image detection element, and second image acquisition that acquires image data in multi-pixel units of the radiographic image detection element.

* * * * *